United States Patent [19]

Glaus et al.

[11] Patent Number: 5,737,076

[45] Date of Patent: Apr. 7, 1998

[54] METHOD AND APPARATUS FOR DETERMINING SUBSTANCES AND/OR THE PROPERTIES THEREOF

[76] Inventors: Ulrich Walter Glaus, Grossensteinstr. 1, CH-8620 Wetzikon; Martin Labhart, Guldistudst. 29, CH-8630 Tann-Ruti; Heinz Wagner, Kleinalbisstr. 33, CH-8045 Zurich, all of Switzerland

[21] Appl. No.: 473,743

[22] Filed: Jun. 7, 1995

Related U.S. Application Data

[63] Continuation of Ser. No. 159,129, Nov. 30, 1993, abandoned.

[30] Foreign Application Priority Data

Dec. 1, 1992 [CH] Switzerland ............... 3704/92
Mar. 18, 1993 [CH] Switzerland ............... 829/93

[51] Int. Cl.$^6$ .................................. G01N 21/27
[52] U.S. Cl. ............ 356/310; 356/326; 356/328
[58] Field of Search ............... 250/226; 356/328, 356/310

[56] References Cited

U.S. PATENT DOCUMENTS

| | | | |
|---|---|---|---|
| 3,210,552 | 10/1965 | Young | 250/226 |
| 4,193,691 | 3/1980 | Fjarlie | 356/330 |
| 4,278,538 | 7/1981 | Lawrence et al. | 250/226 |
| 4,394,069 | 7/1983 | Kaye . | |
| 4,800,279 | 1/1989 | Hieftje et al. | 250/339 |
| 4,914,719 | 4/1990 | Conlon et al. | 250/339 |
| 5,090,807 | 2/1992 | Tai | 356/310 |
| 5,142,151 | 8/1992 | Varnell et al. | 250/339 |
| 5,457,319 | 10/1995 | Moe et al. | 250/339.12 |

FOREIGN PATENT DOCUMENTS

| | | |
|---|---|---|
| 0 354 298 | 4/1989 | European Pat. Off. . |
| 0354298 | 4/1989 | European Pat. Off. . |
| 1 547 358 | 7/1966 | Germany . |
| 1547358 | 7/1966 | Germany . |
| 37 43 584 | 12/1987 | Germany . |
| 3743584 | 12/1987 | Germany . |
| 39 01 825 | 1/1989 | Germany . |
| 3901825 | 1/1989 | Germany . |

OTHER PUBLICATIONS

Millan et al "Dispersine Correlation Spectroscopy: A Study of Mask Optimization Procedures", Applied Optics, vol. 16, #6, Jun. 1977, pp. 1609–1618.
Tran et al "Acousto–Optic Tunable Filter as a Polychromator and Its Application in Multidimensional Fluorescence Spectrometry" Analytical Chemistry, vol. 64, No. 22, Nov. 15, 1992, pp. 2775–2782.
Database WPI Week 8816, 21 Apr. 1988, Derwent Publications Ltd., London, GB; AN 88–111068 & SU–A–1 339 469 (Moscow Lomonosow) 23 Sep. 1987 *Abstract*.
Database WPI Week 9037, 24 Oct. 1990, Derwent Publications Ltd., London, GB; AN 90–281159 & SU–A–1 525 649 (Kuznetsov) 30 Nov. 1989 *Abstract*.
Analytical Chemistry, Bd. 64, Nr. 20, 15 Oct. 1992, pp. 971A–981A, Tran "Acousto–Optic Devices", p. 980A*.

*Primary Examiner*—Vincent P. McGraw
*Attorney, Agent, or Firm*—Antonelli, Terry, Stout, & Kraus, LLP

[57] ABSTRACT

The invention relates to a procedure for determining an identification of a sample of material, or its properties. Electromagnetic radiation from a radiation source (1) is reflected or transmitted through the sample. The radiation from the sample is collected and analyzed over several channels (7, 7', 7"), which modulate the radiation with a spectral transmission function which is unique for each channel. The modulated radiation is transmitted to one or several detectors (9, 9', 9") which produce output signals which are further electronically processed. The spectral range of each of the individual channels is common to all of the channels. Within the common range the channels are provided with different spectral transmission functions (7, 7',7") which are optimally chosen for a given application.

29 Claims, 7 Drawing Sheets

METHOD AND APPARATUS FOR DETERMINING SUBSTANCES AND/OR THE PROPERTIES THEREOF

This is a Continuation Application of U.S. Ser. No. 08/159,129, filed Nov. 30, 1993 now abandoned.

BACKGROUND OF THE INVENTION

1. Field of the invention

The present invention is directed to a method for determining substances and/or the properties of such substances, wherein radiation from a sample is collected and analyzed by a plurality of measuring channels.

It is further directed to an apparatus for determining substances and/or their properties of the type which comprises several measuring channels to which radiation from a sample of the substance is directed.

2. Description of prior art

Common filter spectrometers, such as Infralyzer 450 of Bran & Luebbe, are usually equipped with interference filters, each filter (channel) having a different, usually very narrow spectral transmission range. One disadvantage of instruments with interference filters is that for the identification of n substances, each having an absorption band of a unique specific wave length, n interference filters are required.

Another known type of filter instrument known as the non dispersive correlation filter instrument which is used for IR gas analytics, e.g. the IR-Analyzer of Leeds & Northrup directs the spectrum of the investigated substance onto the calibration radiation. Since these instruments have a wider spectral range than the above mentioned interference filter spectrometers, they have a lower detection limit. However, they are however less because spectra of various different substances such as all fluids and solids are generally strongly overlapping which leads to undesirable cross contamination signals.

SUMMARY OF THE INVENTION

It is an object of the present invention to provide a method and apparatus which eliminates the disadvantages of the prior art method and apparatus and succeeds in getting a particularly high selectivity with a wide spectral range. This object is resolved by the method for determining substances and/or properties thereof, wherein the radiation from a sample of the substance is collected and analyzed by several measuring channels, which method comprises the steps of directing the radiation through the plurality of measuring channels, modulating the radiation in the measuring channels by predetermined spectral transmission characteristics and generating channel specific signals according to the radiation modulated in the respective channels, processing the channel specific signals for determining the substance of the sample and/or its properties and thereby selecting the spectral transmission characteristics of the measuring channels to cover a common spectral range while being different within this common spectral range.

An apparatus which fulfils the above mentioned object comprises a plurality of measuring channels to which the radiation from the sample of the substance is directed, with each measuring channel comprising a predetermined spectral transmission characteristic for modulating the radiation and generating an output signal according to the radiation modulated by the channel specific transmission characteristic.

The apparatus further comprises a processing unit to which the signals according to the modulated radiation are directed. The spectral transmission characteristics of the measuring channels overlap in a common spectral range and are different within this common spectral range.

Thus, according to the present invention, the spectral transmission characteristics, further also named spectral transmission functions, are chosen such that the electromagnetic spectrum of a sample to be measured generates signals that are in direct relationship to the wanted information.

If measuring channels are referred to in the following description, they are to be understood as being associated with just one transmission function if nothing else is mentioned.

In a first preferred embodiment, the radiation is directed through at least a part of the measuring channels in parallel.

In a second preferred embodiment, the spectral transmission characteristic of at least one channel is varied in time, which leads to realization of at least a part of the measuring channels varying sequentially in time. This may be done for example by provision of a matrix of selectively controllable optical switches, e.g. an LCD-screen, or of a matrix of detector elements that can be selectively activated.

In a further far preferred embodiment of the inventive method, properties and/or substances to be determined are predetermined, then the differences of the spectral transmission characteristics are determined in a spaced states. The dimension of the spaced states is equal to the number of measuring channels. Each substance and/or property to be determined defines therein a unique state. Each state within said state space is defined by the integral over all wavelengths of the spectral range of the radiation weighed by the spectral transmission characteristics.

By this preferred operation the inventive method becomes significantly faster compared with common indirect methods of the prior art methods which obtain the data in two steps: The first step comprises measuring the spectrum of a sample with a spectrometer, either dispersevely or via the Fourier transform of an interferrogram. The second step is the extraction of information from this spectrum by means of a method, e.g. principal component analysis or partial least square, which takes into account the full spectrum.

This is normally attained by computationally multiplying the measured spectrum with numerical functions. Then, by computational integration over all wave-lengths, there is obtained for each function a measuring value derived from the spectrum that is directly related to the property under investigation.

According to the present invention the mentioned numerical function and computationally multiplication thereof is replaced by optical acting transmission functions and optical treatment of the radiation, so that spectral measurement and aforementioned computational multiplication and integration is inventively performed optically, which drastically reduces hardware requirements and processing time.

In a further preferred embodiment, polarization interference filters are provided for the achievement of the transmission characteristics with the definite advantage that any transmission characteristic can be realized with little effort. Nevertheless, it is absolutely possible to realize the spectral transmission characteristics by thin interference layer filters.

Even a mixture of thin interference layers and polarization interference filters may be used dependent upon the intended application of the inventive method or apparatus.

In a further preferred mode, the transmission characteristics are simply achieved instead of or in addition to by use of thin layer interference and/or polarization interference filters, by achieving a spectral transmission characteristic a polychromator with masks in the plane of the spectrum, thereby preferably realizing the polychromator with the masks by a matrix of selectively controllable optical switch with an LCD-screen or by a matrix of detectors which can be selectively activated.

Through use of a matrix of selectively controllable optical switches the highest flexibility is reached with respect to time modulation of the spectral transmission functions and/ or with respect to use with different detecting applications.

Furthermore, providing a matrix of detectors that can be selectively activated results in the separate detector arrangement being obsolete. The radiation modulation by means of transmission characteristics and the detection of the modulated radiation occurs simultaneously by the selective activation of detectors.

By preferably modulating at least one of amplification and of spectral position of at least one of the spectral transmission characteristics in time, e.g. imposing a time modulation on a fixed modulating frequency, the resulting signal becomes an AC signal which can be further processed in a frequency selective way on the modulation frequency, to filter out any disturbances. If, for example, the spectra of two substances are in the spectral range of interest of similar intensity, but of different functional forms, then the time modulation over the wave-lengths with the aforementioned functional forms results, as a consequence of the creation of higher order frequencies, in a better selectivity based on a frequency selection criterium.

By different time modulation to realize the different measuring channels, with only one detector it is possible to build the measuring channels merely by assigning a specified frequency to respective measuring channels and electrically select a frequency.

By controlling at least one of the transmission characteristics electro-optically, it further becomes possible use the method for different applications or to use a time multiplex operation over just one single channel. A simple way of time multiplexing is mechanically varying the position of a mask relative to the position of a polychromator which results in mechanical implementation of time modulation.

A further simple and preferred mode of modulation is by means of an acousto-optical modulator and masks.

It is further proposed in a preferred mode of the invention to provide a scaling channel with a substantially constant, non vanishing spectral transmission characteristic and determining at the respective measuring channel a reference output signal occurring at non sampling condition and further determining a reference signal at the scaling channel for this non sample condition. Then the quotient from the reference signal of the specific measuring channel and the reference signal of the scaling channel is formed and the output signal of the scaling channel is scaled with this quotient. From the output signal of the respective measuring channel the output signal of the scaling channel scaled by the this quotient is substracted. There is established in a preferred way the relationship between the predetermined transmission characteristic differences to the optically realizable transmission characteristics.

It is a further object of the present invention to propose a method for producing polarization interference filters. This method comprises the steps of predetermining a spectral transmission characteristic to be realized, direction a linearly polarized electromagnetic field through several plates which are birefringent perpendicular to propagation direction of the field, selecting the thickness of the plates so that the spectral transmission characteristic has a prescribed spectral bandwidth, rotating the optical axis of each plate and providing behind the birefringent plates a polarizator so that the electromagnetic field emanating from the polarizator has an energy spectrum which corresponds to the desired predetermined transmission characteristic.

It is a further object of the present invention to provide a method for scaling several spectral signals that originate from the same signal source and which are differently spectrally weighed and are preferably integrated over at least one spectral degree of freedom. This method comprises the steps of providing the spectral weight of one of the signals to be spectrally constant, providing a scaling signal source and forming the quotient of each of the remaining spectral signals and the one signal, for scaling a signal source input, then multiplying the quotient with the one signal, forming a scaled signal of each of the remaining signals by substracting the result of the multiplication from a respective one of the remaining signals.

The method of scaling is most suitable to be applied with the method and apparatus for determining substances according to the first object of the present invention, but may also be used for other purposes and thus is not limited to a combination with the aforementioned determining method and apparatus.

Especially the last mentioned scaling method last mentioned may clearly be applied to prior art methods and apparatus which were discussed above for determining substances and properties thereof.

Thus, the invention uses special filters and/or adaptively changeable filters, hence basically "filter states" which each individually modulate the radiation in one and the same spectral range in arbitrarily prescribed ways. It thereby needs e.g. for the distinction of 'n' different substances, only a number m of filters and channels equal to log n, and thus drastically reduces the expenditure compared to the common state of the art technology.

Furthermore, the instrument based on the invention offers for quantitative analysis a higher selectivity, but and also a significantly higher signal-to-noise ratio because of its wide spectral range. Such method and apparatus may be used in various technical fields, such as e.g. photography, illumination techniques, pyrometry, colourmetrics, graphical and textile industry, and above all in the chemical analysis of substances either qualitatively for identification or quantitatively for concentration determination.

BRIEF DESCRIPTION OF THE DRAWINGS

The present invention will be better understood and objects other than those set forth above will become apparent when consideration is given to the following detailed description thereof.

Such description makes reference to the annexed drawings.

The figures show:

FIG. 1 shows for the comprehension of the fundamental principle of the procedure of the present invention.

FIG. 2 is a diagram embodiment of an instrument according to the invention.

FIG. 3 is a diagram of another embodiment of an instrument according to the invention.

FIG. 4 is a diagram of a polarization interference filter for creation of transmission functions used in instruments according to the invention.

FIG. 5 is a diagram of a polarisation interference filter, whose transmission function can be modulated by application of electrical fields.

FIG. 6 is a diagram of a polychromator with masks for generating transmission functions for instruments according to the invention.

FIG. 7 is a diagram of another embodiment of an instrument according to the invention, which functions in compliance with the procedure according to the invention, in a further form of realisation.

DESCRIPTION OF PREFERRED EMBODIMENTS

Figure 1:
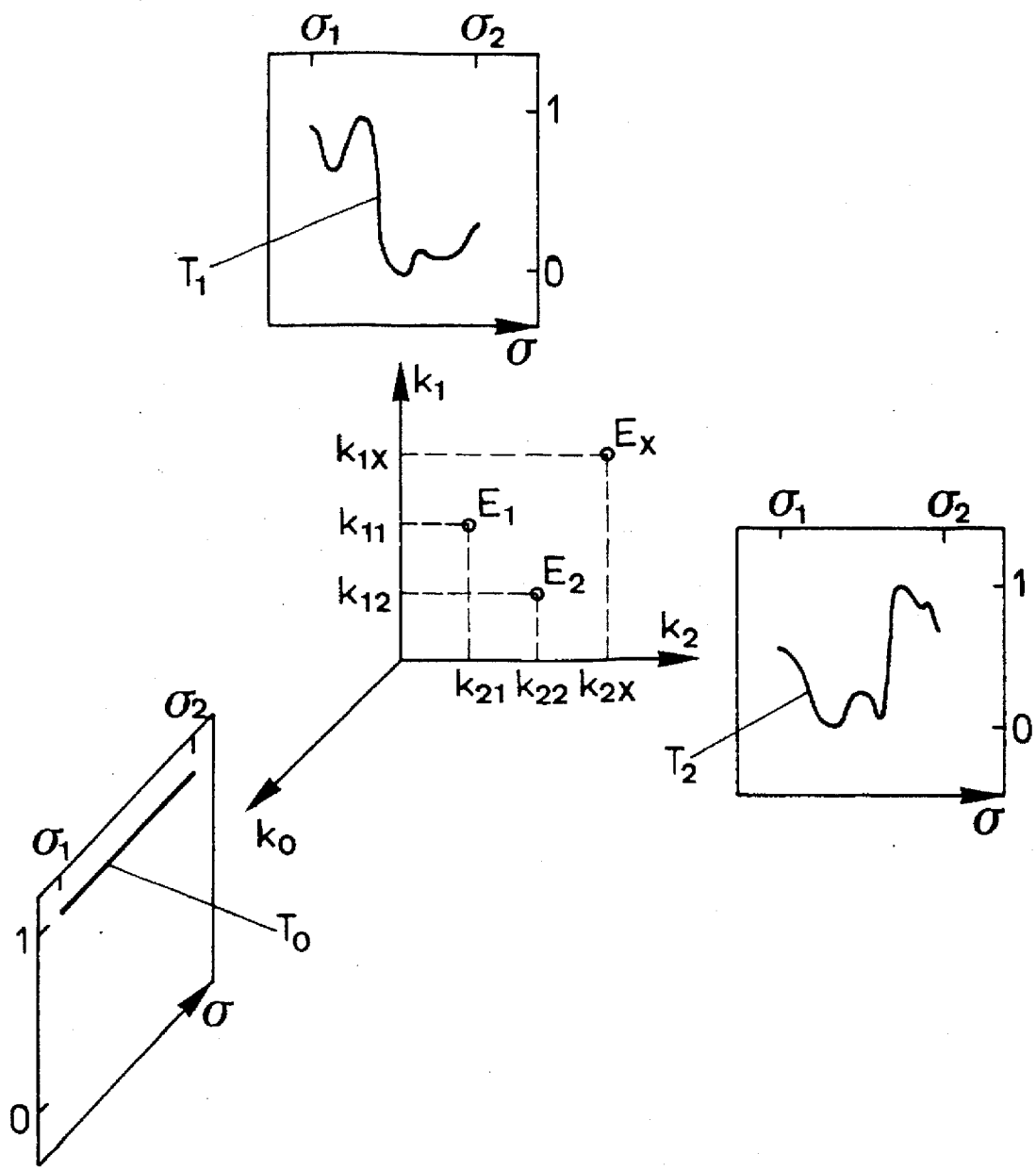

FIG. 1 provides an explanation of the procedure of the invention the three cartesian coordinates $k_0$, $k_1$, $k_2$ symbolize three measuring having transmission functions correspondingly designated by $T_0$, $T_1$, $T_2$. All channels refer to the same spectral range [$\sigma_1$, $\sigma_2$] and the transmission functions $T_i$ (i=0, 1, 2) are presumed to be normalized. The coordinate $k_0$ corresponds to the intensity measuring channels and its transmission function $T_O$ is assumed to be constant. The spectrum of the radiation to be measured in each channel i is multiplied by its transmission function $T_i$ and thereafter by detection of the resulting radiation, channel specifically integrated over all wave-lengths of the spectral range [$\sigma_1$, $\sigma_2$]. The detected channel signal yields a unique coordinate position on the coordinate axis $k_i$ corresponding to channel i.

The depicted three dimensional system can be generalized to any dimension $d \geq 2$.

The measuring channel corresponding to channel $k_0$ is used for normalizing scaling purposes as will be explained below.

If a property $E_1$ to be detected corresponds to channel specific coordinate positions $k_{11}$ and $k_{21}$ and a further property $E_2$ to $k_{12}$ and $k_{22}$, then these are initially determined and stored. The resulting $k_{xy}$-values of a sample under investigation will then be compared to the stored values and it is then determined whether the sample posesses either $E_1$ or $E_2$.

Generally, to each property will be attributed a whole region of position values, the region being determined with statistical methods from a multitude of samples possessing this property. For the reliable determination of different properties one naturally has to suppose that regions attributed to different properties do not have points in common.

In the case a property (e.g. water content) can take a continuous range of values, it may be an advantage to determine the property value of an unknown sample by interpolation or extrapolation in the most general sense from the property values of samples that have initially been determined.

Figure 2:
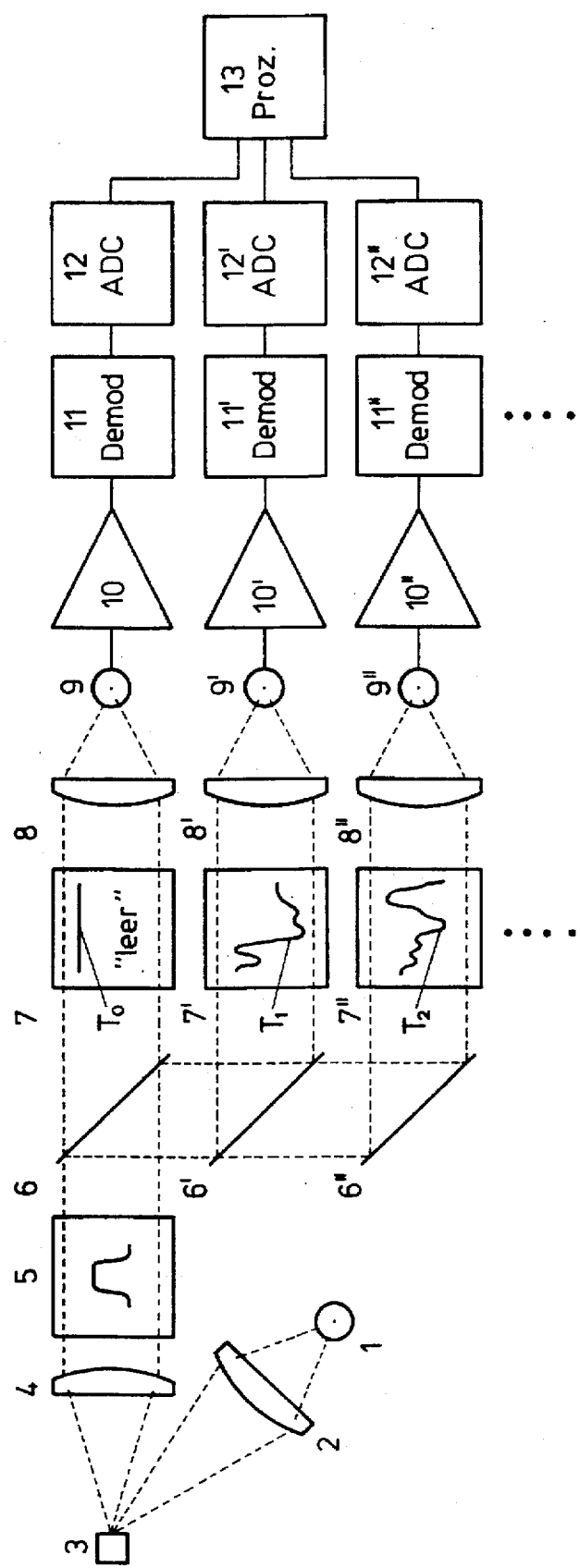

FIG. 2 shows an embodiment of an instrument according to the invention. With electromagnetic radiation of a generically broad band source 1 and an optical arrangement 2, shown here as a lense, a sample 3 to be investigated is illuminated. An optical arrangement 4, shown here as a lense, collects the radiation from the sample and transforms it into a beam that may be directed through a (not absolutely necessary) filter 5 to restrict the spectral range to [$\sigma_1$, $\sigma_2$] according to FIG. 1. The beam is then, as exemplified here by the beam splitters 6, 6', 6", divided in to the different channels. The partial beams pass through the optical elements 7, 7', 7", here exemplified by polarisation interference or ordinary interference filters, will, by means of the transmission functions T, be spectrally and possibly time modulated. One of the channels 7 serves as an intensity measurement channel according to FIG. 1. The optical arrangements 8, 8', 8", here shown as lenses, focus the partial beams onto detectors, respectively converters 9, 9', 9". The electrical signals leaving the detectors 10, 10', 10", are amplified eventually time demodulates 11, 11', 11", converted from analog to digital by A/D converts 12, 12', 12" and transmitted to a processor 13, that calculates from the signals, corresponding to the kxy-values of FIG. 1 the result as will be described below.

The optical arrangements represented as lenses, 2, 4, 8-8" can also be mirrors or fiber optical arrangements or combinations thereof. The division of the beam can be accomplished not only by beam splitters, but also by fiber optics. It is not absolutely necessary that each partial beam be focussed onto a seperate detector; with an optical multiplexer the partial beams can be focussed onto one single detector. It is also possible to modulate the amplitude of each transmission function at a different frequency, for instance with the help of Kerr cells, such that the signals can be monitored with only one detector and later be divided by frequency switches into the different channel specific signals. This results in saving of detectors and electronic components. Only one radiation transmission channel can be used, e.g. 4, 5, 6, 7, 8, 9 by adaptively changing the filter element 7, forming the transmission functions of the different channels sequentially. As an changeable filter element, a matrix of selectively controllable optical switches behind a polychromator can be employed, e.g. an LCD screen. If a matrix of detector elements, that can be selectively activated, is provided behind a polychromator, the detector 9 and the filter element 7 are implemented simultaneously.

Figure 3:
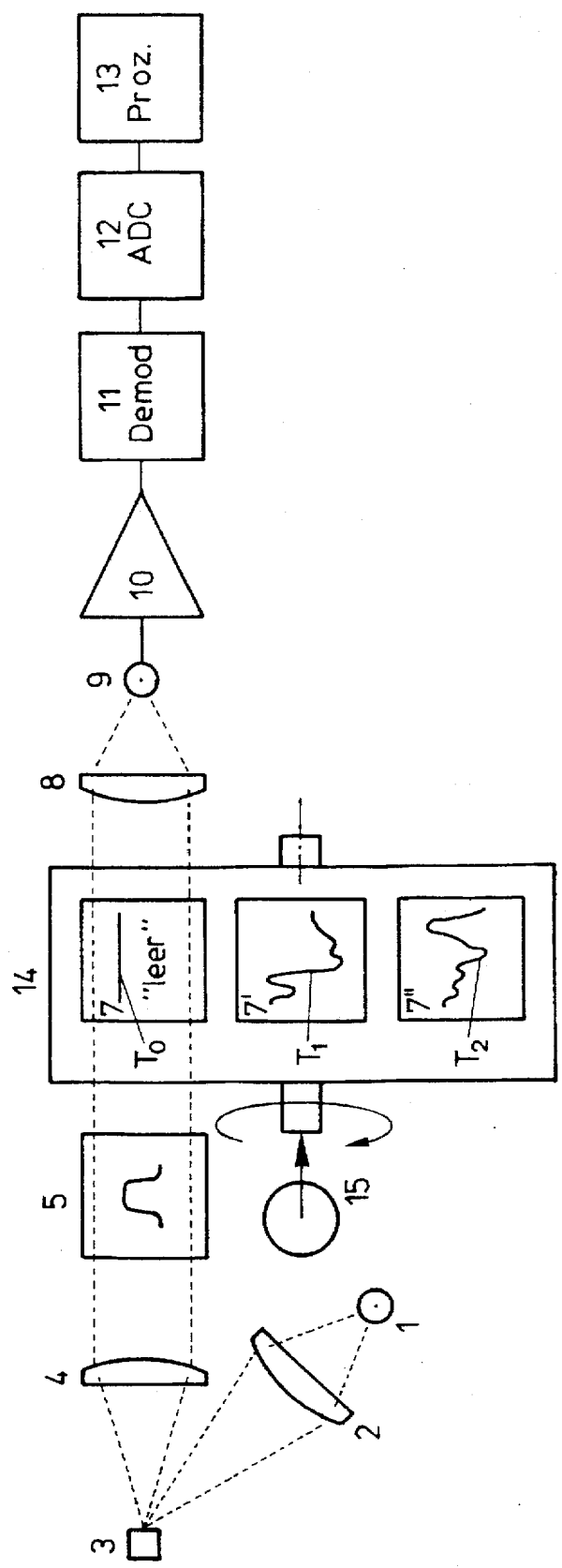

A saving in optical components is achievd with the possible implementation of the instrument according to the embodiment shown in FIG. 3. Here the filters 7, 7', 7" of the embodiment of FIG. 2 with diferent transmission functions are moved into the measuring beam 14 with a mechanical drive 15.

Figure 4:
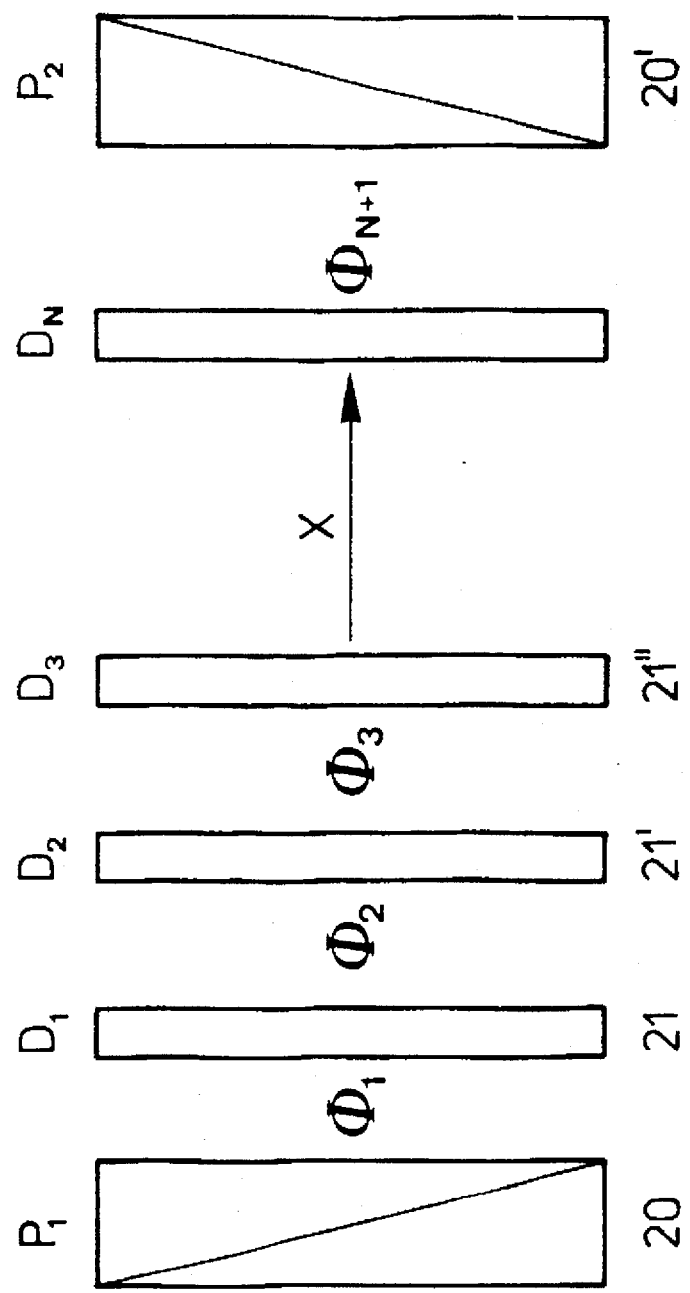

FIG. 4 shows a preferred embodiment of the polarization interference filters used in the invention. Elements 20 and 20' are polarizers; elements 21, 21', 21" ... are plane parallel birefringent plates, whose dielectric axes are in a predetermined orientation to each other and to the transmission directions of the polarizers, such that the desired spectral transmission function is generated. The order polarizers-birefringent plates—polarizers may be altered additional polarizers can be placed between the birefringent plates, with the disadvantage however, that the transmission of the filters is reduced.

Figure 5:
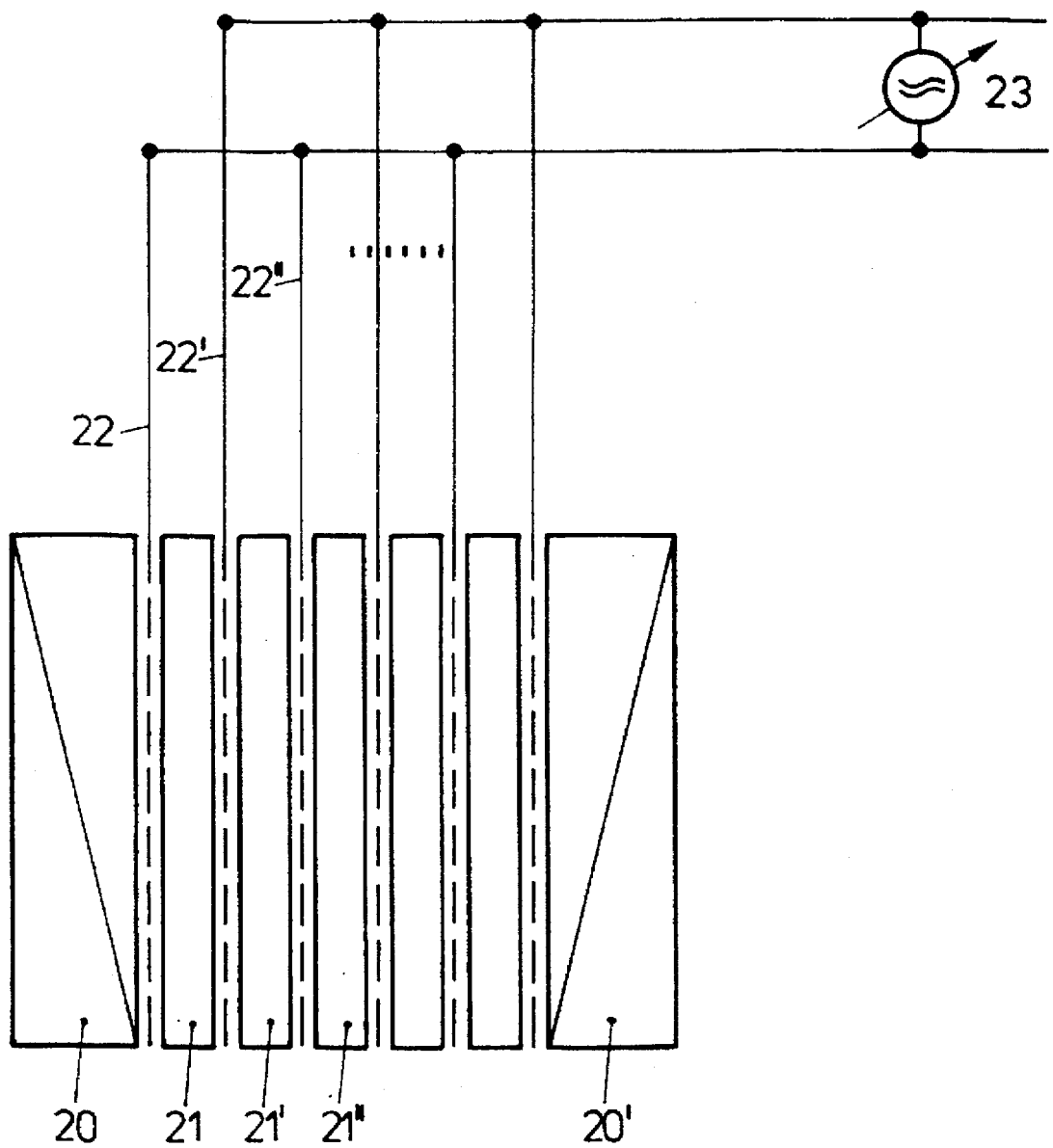

FIG. 5 shows a preferred embodyment for the time modulation of the spectral transmission functions of polarization interference filters. At the arrangement exemplified here by the electrodes 22, 22', 22" ... longitudinal, time variable electrical fields can be applied with a voltage source 23. These fields change the birefringence of the plane parallel plates and thereby induce a time modulation. The electrical fields do not necessarily have to be longitudinal; it is also possible to apply transversal electrical fields by installing the electrodes at the edges of the birefringent plates. By suitable circuitry it becomes possible to tune the electrical field and consequently the birefringence of each plate individually which enables tuning of the spectral range of the transmission function.

Figure 6:
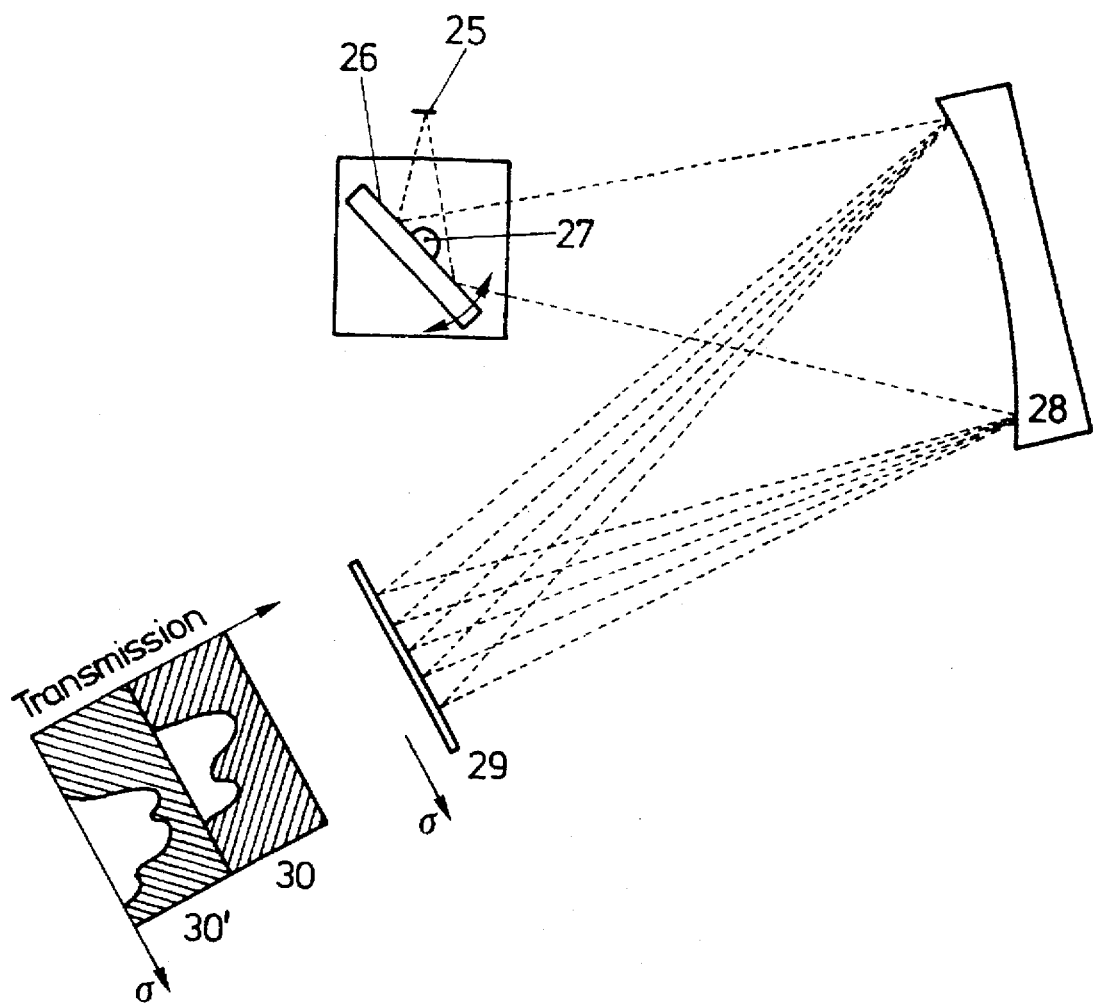

FIG. 6 shows a preferred embodiment of the optical instrument according to the invention, which uses a polychromator with masks to generate the transmission functions. An image of the radiation coming off the sample is formed on the entrance slit 25 of a polychromator. The radiation then passes an optical deflection system that allows for translation of the position of the image of the entrance slit, here exemplified by a deflection mirror 26 fixed to the axis of a galvanometer coil 27. The concave diffraction grating 28 chosen here as an example for a dispersing an optical element generates the spectrally resolved image of the entrance slit in the image plane 29. In this plane, masks are attached vertically to the drawing plane, each of which generates a prescribed transmission function. As illustrated, the transmission function has a spectral band pass of two bands of higher transmission separated by a band of lower transmission. The masks can for instance be blinds 30, 30'..., where one transmission function is supposed to be the intensity measurement channel, i.e. its transmission function is a constant. The radiation leaving each mask is then focussed onto a detector to generate the desired signal. By periodically moving the deflection mirror 26 the transmission functions can be time modulated.

In addition to a swinging mirror on a galvanometer coil, transparent plates and prisms with other drives can be considered as modulators. Time modulation is also achieved by moving the grating 28 around its center point or by rotating a dispersion prism or by translating the masks 30, 30'... in the focal plane. The masks can also be neutral filters with variable optical transmission or a liquid crystal array, for which the transmission of each pixel can be tuned by application of an electric field allowing in addition a time modulation without mechanically moving parts.

Figure 7:
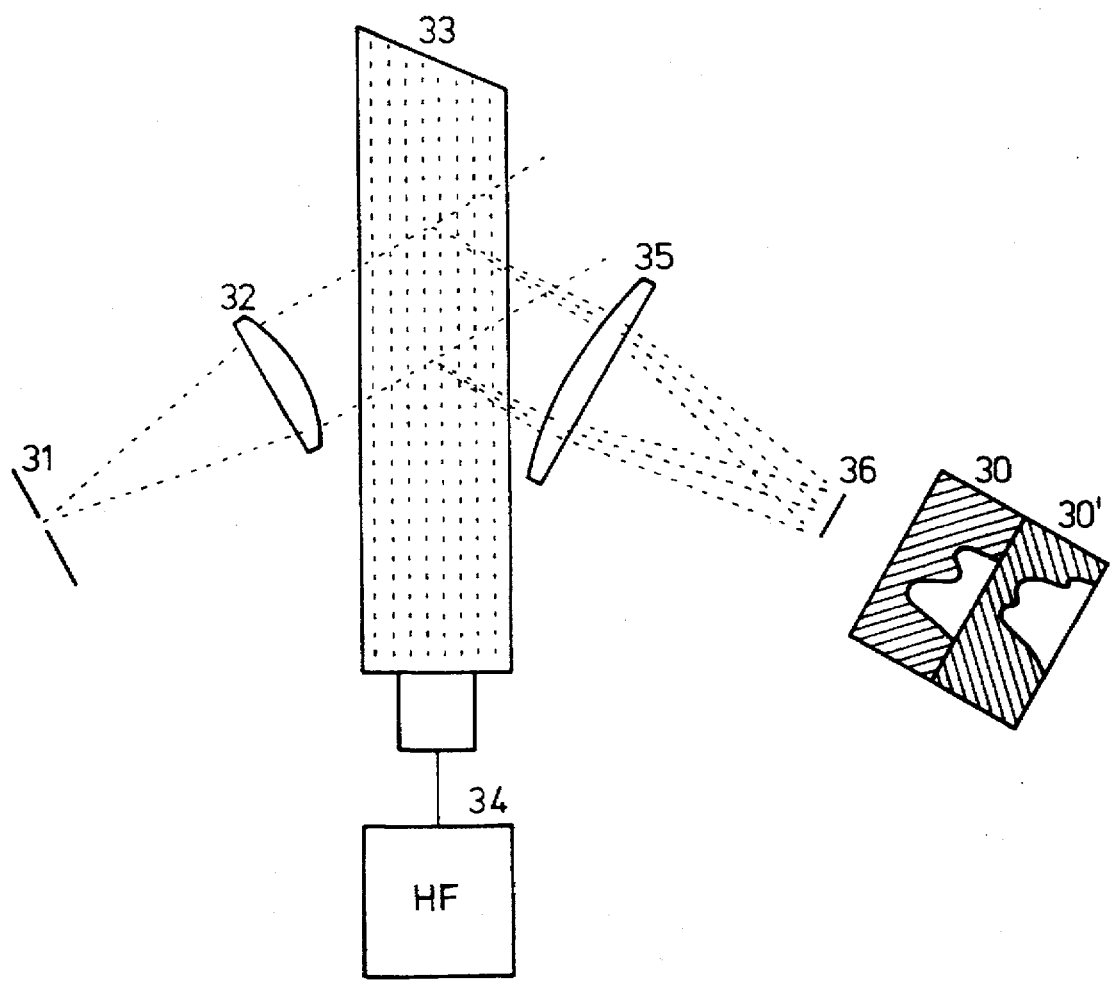

FIG. 7 shows an embodiment of a optical instrument according to the invention which utilizes an acoustooptic modulator as dispersing element. Together with the masks 30, 30' the spectral transmission functions are then generated. The radiation off the sample enters through the slit 31; with the collimator, shown here as generating a lense, a parallel beam, which is diffracted by the standing acoustical waves of a transparent medium. The medium 33 can be a tranparent solid or a cuvette filled with a transparent fluid or gas. A HF-driver 34 generates the acoustical waves in the medium. An optical arrangement 35, exemplified here as a lense, focuses the diffracted radiation into the plane 36, where as described above (FIG. 6) masks 30, 30'... are attached vertically to the drawing plane. By variation of driving HF-Frequency a time modulation can be obtained.

The invention is among other things concerned with a method, where a radiation source with spectrum $S(\sigma)$, $\sigma$ having the wavenumber in $cm^{-1}$, emits radiation that is either transmitted through or reflected off the sample. The sample itself can also emit radiation or be excited to emit radiation in another frequency range. The radiation coming from the sample is then collected by the instrument through suitable optics, possibly being modulated by a filter with spectral transmission $F(\sigma)$ and then seperated into several channels, of which each has its own transmission function $A_k(\sigma)$, k designating the specific channel. After passage through channel k, the radiation is directed to a detector with spectral sensitivty $\Gamma(\sigma)$.

A further possible arrangement provides for a diffusely reflecting screen with reflection spectrum $R(\sigma)$ behind the sample allowing measurement of transparent and diffusely reflecting samples with the same arrangement.

By the presence of a sample with a transmission (resp. reflection a spectrum $I(\sigma)$ (always supposed to be divided by the reference spectrum obtained by when no sample is present), the electric signal measured by the detector after channel k is then proportional to $$W_k = \int K(\sigma)I(\sigma) A_k(\sigma)d\sigma, \tag{1}$$

where the function $K(\sigma)$ is formed from all spectral influences in the absence of a sample, e.g by the product of $S(\sigma)$, $\Gamma(\sigma)$ and, as the case may be, also $F(\sigma)$ and $R(\sigma)$ plus further spectral influences not mentioned here.

The spectral transmission functions $A_k(\sigma)$ are to be chosen such that they have optimal properties for a given application.

A preferred method is to obtain of each sample n its wave-length resolved spectrum $I_n(\sigma)$. These spectra are usually measured with respect to a reference. In other words they are divided by the spectrum obtained by a fixed given arrangement of the radiation source, the instrument and possibly the reflector in the absence of any which results for such spectra $K(\sigma) \equiv 1$ in equation (1) above. For any arbitrary arrangement $K(\sigma)$ can then be determined by a corresponding reference measurement and then with the use of equation (1) the signal to be expected with the instrument according to the invention can be determined in the various channels for each sample.

Channel 0 is from now on defined to be the intensity measurement channel with its transmission function always being understood to be $A_0(\sigma) \equiv 1$.

For the further calculations it is preferable to subtract the constant part of the spectra. Therefore the following relationships exist:

$$I_{0n}(\sigma)=I_n(\sigma)-C_n, \text{ such that} \tag{2}$$

$$\int K(\sigma)I_{0n}(\sigma)d\sigma=0. \tag{3}$$

Furthermore, let $w_{kR}$ be the signal measured in the absence of a sample in Channel k. Therefore $$0=\int K(\sigma)(I_n(\sigma)-C_n)d\sigma=W_{0n}-C_nW_{0R}, \text{ e.g. } C_n=W_{0n}/W_{0R}. \tag{4}$$

New spectra are now obtained from the spectra $I_{0n}(\sigma)$ by multiplication with the function $K(\sigma)$ $$J_n(\sigma)=K(\sigma)I_{0n}(\sigma). \tag{5}$$

Up to an additive constant, the spectral transmission functions $A_k(\sigma)$ are then computed from the spectra $J_n(\sigma)$ by singular value decomposition for example or by Principal Component Analysis (K. V. Mardia, J. T. Kent, J. M. Bibby: Multivariant Analysis, Academic Press, 1979). The spectral transmission functions can also be obtained by other means, e.g. Partial Least Squares (H. Martens and T. Naes: Multivariate Calibration, J. Wiley & Sons Ltd, 1989) or with pure estimation.

Each spectrum $J_n(\sigma)$ is then approximated by its components $$V_{kn}=\int U_k(\sigma)J_n(\sigma)d\sigma \tag{6}$$

with respect to the "factors" $U_k(\sigma)$, e.g.

$$J_n(\sigma) = \sum_{k=1}^{K} V_{kn}U_k(\sigma) + R_n(\sigma) \tag{9a}$$

K signifies here the number of channels in addition to the intensity measuring channel. The factors $U_k(\sigma)$ are chosen such that they are maximally correlated with the properties under investigation. The residual $R_n(\sigma)$ not described by the factors is supposed to be irrelevant for the application considered.

It follows from the singular value decomposition that the spectral distributions, also called "factors", are pairwise orthogonal, which means that $$U_{k1}(\sigma)U_{k2}(\sigma)d\sigma=0, \text{ if } k1 \text{ not equal to } k2. \quad (7)$$

Equation (7) can only be satisfied if negative values are allowed for $U_k(\sigma)$. Obviously, it is desirable to identify the calculated factors with the transmission functions of the procedure according to the invention; however, the transmission functions are certainly always positive. To obtain a relation between the measured quantities $W_{kn}$ defined in (1) and the theoretical factor components $V_{kn}$ defined in (6), $$a_k = \min U_k(\sigma) \quad (8)$$

If $A_k(\sigma)$ is now chosen such that $$\int U_{k1}(\sigma)U_{k2}(\sigma)d\sigma = 0, \text{ if } k1 \text{ not equal to } k2. \quad (7)$$

then the relation below can certainly be satisfied with constant $b_k$ $$U_k(\sigma)=b_k(A_k(\sigma)+a_k) \quad (9)$$

What is now the precise connection between the measured values $W_{kn}$ defined in (1) and the components $V_{kn}$ defined in (6)?

From (2), (4), (5), (6), (8), (9) it is deduced that $$V_{kn}=b_k\int(A_k(\sigma)+a_k)K(\sigma)(I_n(\sigma)-C_n)d\sigma=b_k\int A_k(\sigma)K(\sigma)(I_n(\sigma)-C_n)d\sigma+ b_ka_k\int K(\sigma)(I_n(\sigma)-C_n)d\sigma=b_k(W_{kn}-(W_{kR}/W_{OR})W_{On}) \quad (10)$$

It follows therefore that with the help of an intensity measurement channel and a reference measurement in the above mentioned sense, an exact relation can be established between the factor components of a sample and the signal it generates in the corresponding channels in the instrument according to the invention.

For certain applications, e.g. for the identification of chemical compounds, the absolute magnitudes of the $V_{kn}$ are not necessarily of the greatest relevance, but rather the relative quotient for the different channels K is of the greatest intent. In this case it desirable to normalize $V_{kn}$ to one; for instance by introducing new quantities $X_{kn}$ that are defined by $$X_{kn} = V_{kn}/\left(\sum_{k=1}^{K} V_{kn}^2\right)^{1/2} \quad (11)$$

where K is the number of channels (without the intensity measurement channel). It can then be expected that samples of identical chemical composition will, independently of their reflection- or transmission properties, be very closely spaced with respect to the $X_{kn}$.

The purpose of the present invention is, as already mentioned, the fast, direct and precise determination of the measurement signal with a simple, robust instrument.

In a preferred embodiment the instrument comprises the following previous described components:

1. In the case of a sample that does not emit radiation by itself, a radiation source is focussed onto the object under investigation with an optical arrangement having mirrors and/or lenses. To prevent the object from overheating by absorption of too much radiation, the radiation source can be switched on and off, pulsed or modulated. In the case of a continuous radiation source, overheating can be prevented by interrupting or deflecting the radiation beam. For this purpose, mechanical and optical systems such as shutters and choppers, movable blinds and deflection optics, rotating polarizers and optical switches can be used. If the beam is interrupted or modulated periodically, then these devices can also be used to time modulate the signals.

2. Collection optics pick up the radiation reflected, transmitted or emitted by the sample, and directs it onto the different radiation transfer channels. For collection, the common optical arrangements such as mirrors, lenses and fiber optics can be used and for the direction onto the the radiation transfer channels various forms of beam splitters and fiber optics may be used.

3. In the plurality of radiation transfer channels, the radiation is modulated by filters with prescribed spectral transmission functions. This process has two parts: Selection of a spectral range and creation of the spectral transmission function within this range. Both parts can, as the case may be, be provided by several filters at one or various locations in the beam path.

The spectral range of interest can be selected with known methods, such as:

the radiation source emitting only in the range of interest;
the detector has a corresponding spectral sensitivity;
Polychromators with prisms and/or gratings;
acoustooptical filters;
interference filters;
cut off filters such as colored glasses, dichroitic beam splitters, etc.
reflection filters
diffraction at color substances, Christiansen filters;
absorbing fluids and gases; and
polarisation interference filters as described in the following explanation The preferred embodiment to generate the prescribed spectral transmission functions is described below. With a polarization interference filter, within the spectral transmission range of the birefringent material and the polarizers any arbitrary continuous transmission function can be generated.

Let $A_k(\sigma)$ be the spectral transmission function that is to be generated, and let it be restricted to a spectral range corresponding to wave number interval $[\sigma_1, \sigma_2]$. A preferred procedure to generate this transmission function with polarization interference filters demands that it be continued on the wavenumber axis in a mirror symmetrical way, e.g.

$$A_k(2\sigma_2-\sigma)=A_k(\sigma) \text{ for } \sigma\in[\sigma_1, \sigma_2]. \quad (12)$$

With this relationship it becomes possible to generate the desired transmission function by placing identical birefringent plates (e.g. plates made of quartz or calcite or other birefringent materials) between two polarizers. The plates are to be oriented in such a way that perpendicular to the direction of propagation of the radiation to be analyzed, birefringence is taking place. For simplicity, only uniaxial crystals are considered in the following, whose crystallographic symmetry axis, in the following explanation called the optical axis, is assumed to be perpendicular to the direction of propagation of the radiation to be analyzed. Let D denote the common thickness of the plates, and $\mu(\sigma)$ be their generally wave-length dependent birefringence. To simplify further considerations, the variable $u=\mu(\sigma)\sigma$ is introduced. Since $\sigma(\mu)$ is always supposed to be a monotonic function in the spectral range of interest, there is a one to one relation between u and $\sigma$.

Between the interval $[\sigma_1, \sigma_2]$ and the thickness D exists the following relation $$D\, u(\sigma_1)=m/2. \quad (13a)$$

$$D \, u(\sigma 2) = (m+1)/2, \text{ m integer} \tag{13b}$$

Therefore, for a given spectral range the thickness has to be chosen accordingly.

If one such birefringent plate is placed between two polarizers, whose tranmission axes have the same orientation, and the optical axis of the plate makes an angle of 45 degrees with the transmission axis of the polarizers, then a spectral modulation is created that for even m is given by $$M(u) = \alpha(1 + \cos(2\pi D u)). \tag{14}$$

Such an arrangement then leads to a periodic transmission function in the variable u, which for just one plate is a cosine-function with the periodicity in u being equal to $D^{-1}$.

If now N plates are placed between two polarizers, then one obtains in place of a simple cosine the series $$f(u) = \sum_{n=0}^{N} g_n \cos(2\pi D n u) = 1/2 \sum_{n=0}^{N} g_n (z^n + z^{-n}), \tag{15}$$

$$z = e^{2\pi i D u} \tag{16}$$

whereby the coefficients $g_n$ depend on the angles between the optical axes of the individual plates and the transmission axis of the first polarizer. The mirror symmetric continuation of the spectral transmission function defined in (12) guarantees that it can be arbitrarily precisely approximated by a cosine series such as the one in (15). This implies, that the spectral transmission function can be approximated by a Fourier series to any desired precision. In practice, up to 20 plates are completely sufficient for most spectral transmission functions. In the following $f(u(\sigma))$ designates the transmission function $A_k(\sigma)$ in channel k.

Consider the arrangement according to FIG. 4 more closely. The radiation incident onto this arrangement is first linearly polarized by a polarizer $P_1$. It then impinges on a birefringent plate $D_1$, whose optical axis (perpendicular to the direction of propagation of the radiation) is rotated by an angle $\Phi_1$ with respect to the polarization direction. After this the radiation passes further birefringent plates $D_n$ ($2 \leq n \leq N$), whereby the angle between the optical axes of $D_{n-1}$ and $D_n$ is designated $\Phi_n$. At the end, the radiation passes a further polarizer $P_2$, also called an analyzer having a polarization direction which is rotated by an angle $\Phi_{N+1}$ against the optical axis of $D_N$.

The spectral transmission function $f(u(\sigma))$, having a $K(\sigma)$ weighted integral over all wavenumbers is measured by the detector according to equation (1) in the absence of a sample ($I(\sigma) \equiv 1$), corresponds to the energy spectrum of a linearly polarized electromagnetic field, which in the following is further investigated with the help of Jones-matrices. The relation of $f(u)$ to the angles $\Phi_1 \ldots \Phi_{N+1}$ is found by examining the behavior of the field generating $f(u)$. The electrical field component $E = \text{Re}(a_N(z))$ of the field can in complete generality be described by $$f(u) = \left( \sum_{n=0}^{N} a_n z^n \right) \left( \sum_{n=0}^{N} a_n z^{-n} \right) = a_N(z) a_N^*(z). \tag{17}$$

It is to be rated that $$a_N(z) = \sum_{n=0}^{N} a_n z^n \tag{18}$$

is the formula for the relative amplitude of field leaving the embodiment of FIG. 4, which means that the amplitude is divided by the amplitude of the field entering the arrangement through $P_1$. In the terminology using complex numbers it is always understood that physical quantities are obtained by either taking the real or imaginary parts. For the $f(u)$ given by equation (15), $a_N(z)$ can be determined from equation (17) by "polynomial root taking". In general there exist several solutions for which all coefficients $a_n$ ($0 \leq n \leq N$) are real as long as $f(u) \geq 0$ for all u; since $f(u)$ is an electromagnetic energy spectrum, this condition is certainly satisfied.

For the further computations without loss of generality it can be assumed that:

$$\min_u f(u) = 0 \tag{19a}$$

$$\max_u f(u) = 1 \tag{19b}$$

For an electromagnetic wave propagating according to the embodiment of FIG. 4 in the x-direction, the electrical field can be described as a vector $(E_1, E_2)$ in the plane perpendicular to the x-direction. The influence of the embodiment of FIG. 4 on a field entering through $P_1$ can be determined with the help of the transfer matrix $T_N$, which is defined as follows $$\begin{bmatrix} E_{1,out} \\ E_{2,out} \end{bmatrix} = \begin{bmatrix} T_{N,11} & T_{N,12} \\ T_{N,21} & T_{N,22} \end{bmatrix} \begin{bmatrix} E_{1,in} \\ E_{2,in} \end{bmatrix} \tag{20}$$

The (2×2)-transfer matrix therefore maps the incoming field onto the outgoing field. It is composed of the product of Jones-matrices for the individual optical components and simple (2×2)-rotation matrices, which are determined by the angles $\Phi_1 \ldots \Phi_{N+1}$. Vi.z.z.

$$T_N = D R_N D R_{N-1} \ldots D R_2 D R_1 \tag{21}$$

with $$D = \begin{bmatrix} z & 0 \\ 0 & 1 \end{bmatrix} \tag{22}$$

the Jones matrix for a birefringent plate (z being defined in equation (16)) and $$R_n = \begin{bmatrix} c_n & s_n \\ -s_n & c_n \end{bmatrix} \begin{matrix} c_n = \cos(\Phi_n) \\ s_n = \sin(\Phi_n) \end{matrix} \tag{23}$$

a (2×2)-rotation matrix by the angle $\Phi_n$.

It can be shown recursively that $T_N$ depends on z as follows $$T_N(z) = \begin{bmatrix} \sum_{i=1}^{N} a_i^{(N)} z^i & \sum_{i=1}^{N} b_i^{(N)} z^i \\ -\sum_{i=1}^{N} b_{N+1-i}^{(N)} z^{i-1} & \sum_{i=1}^{N} a_{N+1-i}^{(N)} z^{i-1} \end{bmatrix} \tag{24}$$

The connection of the polynomials in the elements of the transfer matrix to the field amplitude of equation (18) is established by projecting out a transfer matrix element with the polarizers $P_1$ and $P_2$ of FIG. 4, Viz.

$$\begin{bmatrix} a_N(z) & 0 \\ 0 & 0 \end{bmatrix} = \begin{bmatrix} 1 & 0 \\ 0 & 0 \end{bmatrix} \begin{bmatrix} c_{N+1} & s_{N+1} \\ -s_{N+1} & c_{N+1} \end{bmatrix} T_N(z) \begin{bmatrix} 1 & 0 \\ 0 & 0 \end{bmatrix} \tag{25}$$

Multiplying out explicitely, the following equation is obtained:

$$a_N(z) = c_{N+1} T_{N,11}(z) + s_{N+1} T_{N,21}(z) \tag{26}$$

whereby $$c_{N+1} = \cos(\Phi_{N+1}), \quad s_{N+1} = \sin(\Phi_{N+1}).$$

The Polynamial $\Sigma b_i^{(N)} z^i$ defined in equation (24) is not independent of the outgoing field $a_N(z)$. It has to be determined in such a way that by rotating the analyzer through 90° the outgoing field will have the complementary energy spectrum $$f^*(u) = 1 - f(u). \quad (27)$$

Physically, this means that in the embodiment of FIG. 4, there is no energy loss between the polarizers $P_1$ and $P_2$ except for absorption in and reflection at the birefringent plates. To determine the rotation angles the fields $a_N(z)$ and $b_N(z)$, which leads to equation (27), have to be computed initially. This leads to the following equations for the coefficients of the polynomials:

$$a_N(z) = \sum_{i=1}^{N+1} a_i^{(N+1)} z^{i-1} \quad (28a)$$

$$b_N(z) = \sum_{i=1}^{N+1} b_i^{(N+1)} z^{i-1} \quad (28b)$$

Equation (28a) corresponds to equation (18), where the summation index has been raised by one and the coefficients have the superscript N+1, because of the now following iterative computation of the angles $\Phi_n$. Equation (28b) designates the coefficients of the complementary field.

For the computation of the angles the following iteration can be used. Set n=N+1 and proceed as follows:

$$\Phi_n = \arctan(b_1^{(n)}/a_n^{(n)}) \quad (29a)$$

$$c_n = \cos(\Phi_n), \quad s_n = \sin(\Phi_n) \quad (29b)$$

$$a_{n-1}^{(n-1)} = a_n^{(n)}/c_n, \quad b_{n-1}^{(n-1)} = -a_1^{(n)}/s_n \quad (29c)$$

$$\left. \begin{array}{l} a_{i-1}^{(n-1)} = c_n a_n - a_i^{(n)} + s_n b_{i+1}^{(n)} \\ b_i^{(n-1)} = -s_n a_{n-i}^{(n)} + c_n b_{i+1}^{(n)} \end{array} \right\} \; 1 \leq i \leq n-2 \quad (29d)$$

The quantity n is always replace n by n−1 and repeat the computations of equation (29a–d) until n=0. In this way all angles $\Phi_n (N+1 \geq n \geq 1)$ are obtained and in addition the fields that occur as elements of the transfer matrix for an arrangement with n birefringent plates.

The desired transmission function can also be generated by other means:

With interference filters not only can the common band pass filters be generated but also, by a suitable choice of the thickness of the interference layers, complicated functions are also generated as needed for the practice of the invention.

With polychromators, that split the measuring beam into a spectrum with a prism, a grating or an acoustooptically generated diffraction grating, the desired transmission functions can be implemented with masks in the image plane of the spectrum.

A mask transmits or reflects at each wave-length a part between 0 and 100% of the radiation intensity.

The transmitted reflected radiation is focussed onto the detector with an optical arrangement. If there are several radiation sources at the entrance slit of the polychromator, for instance vertically placed fiber optics, or if several masks are placed into the image plane of the spectrum and seperately focused onto a detector array or several detectors, then several transmission functions can be implemented with one polychromator.

The mask can be used as a bandpass filter in addition to generating the spectral transmission function. One possible implementation of a mask is a blind with a part below the transmission function being transparent and the part above the transmission function by opaque. The analogous implementation using reflection replaces the transparent part with a reflecting part and the opaque part with a transparent part.

Another embodiment of a mask is a filter, which reduces the intensity at each wave length to the corresponding value of the transmission function. This can be a neutral filter with a spatially variable transmission or a filter, having an arrangement of individual partially transmitting or reflecting having a distribution which generates the desired spectral transmission function.

Another form of a mask consists is an arrangement of optical switches. A common type of switch (LCD) consists of a birefringent material between two polarizers. By application of an electrical or magnetic field the birefringence is altered so that a desired transmission and reflection value can be obtained. By repeatedly switching the element between its on- and off state within suitable time intervals, any transmission or reflection value can be obtained as a time average. This type of mask allows for a great flexibility in generating arbitrary band pass and transmission functions.

4. The time modulation of the intensity or the spectral transmission function is in principle not necessary for the determination of the measuring value but it often improves the precision. Theory and circuitry technology for amplitude and frequency modulation are amply described in the literature and modulation procedures are widely used in measurement technology.

As modulators for electromagnetic radiation the following methods can be considered:

Mechanical systems using rotating sectors with blinds, swinging blinds and deflection optics.

Pulsed and controllable radiation sources with the modulation carried out by the current supply.

Electrooptic modulators using the effect of electrically induced birefringence which are known as Pockels cells, Kerr cells and Piezo modulators.

Magnetooptic modulators utilizing the birefringence induced by a magnetic field known as Faraday and Cotton-Mouton modulators.

Acoustooptic modulators using the diffraction of radiation by sound waves in a medium known as Brillouin, Debye-Sears and Raman-Nath modulators.

5. The detector converts the incoming electromagnetic radiation into an electrical signal. All known types of detectors can be considered such as photo multipliers, photo diodes, photo transistors, photo conductors, photo voltaic cells, pyroelectric detectors, Golay cells, Bolometers and so on.

6. The electronics function as a filter, possibly a demodulator, amplifier and an analog digital converter of the detector signal such that the further processing of the signal according to equations (1–11) can be performed either using hardware or with a processor in software.

We claim:

1. A method for monitoring the presence of a predetermined substance and/or a predetermined property in a sample comprising:
   generating radiation in a predetermined spectral band from said sample;
   monitoring a spectral distribution of said generated radiation with at least one measuring channel including a transmitting filter having a predetermined spectral transmission characteristic throughout said predetermined spectral band;

multiplying with said transmitting filter a signal dependent on said spectral distribution of said generated radiation and a numerical spectral function specific to said predetermined substance and/or property of said sample to generate a signal dependent on said spectral distribution multiplied by said numerical spectral function;

optoelectrically converting said radiation transmitted by the transmitting filter to generate an electric output signal representing energy transmitted by the transmitting filter of said at least one measuring channel; and wherein said electric output signal is dependent on said spectral distribution multiplied by said numerical spectral function, is integrated over said predetermined spectral band and is directly related to said predetermined substance and/or property of said sample.

2. The method of claim 1 further comprising:
directing radiation from an unknown sample in parallel through at least one measuring channel and a reference channel.

3. The method of claim 1 comprising:
varying the transmission characteristic of said at least one measuring channel in time to product time multiplexing of transmission characteristics in said at least one measuring channel.

4. The method of claim 2 wherein:
the output signal of each of measuring channel is produced in response to the predetermined spectral band directed through the at least one measuring channel.

5. The method of claim 1 further comprising:
producing the spectral transmission characteristic of said at least one measuring channel by placement of at least one polarization interference filter therein.

6. The method of claim 1 further comprising:
producing the spectral transmission characteristic of said at least one measuring channel by placement of at least one interference filter therein.

7. The method of claim 1 further comprising:
producing the spectral transmission characteristic of said at least one measuring channel by placement of at least one polychromator having a mask in a plane of the spectral band.

8. The method of claim 7 further comprising:
a matrix of selectively controllable optical switches which function as the at least one polychromator with a mask.

9. The method of claim 7 further comprising:
one of a LCD screen or a matrix of detectors which are selectively activated as the matrix of the at least one polychromator with a mask.

10. The method of claim 1 further comprising:
modulating at least one of amplification and spectral position of at least one of the spectral transmission characteristics in time.

11. The method of claim 1 further comprising:
controlling electrooptically the spectral transmission characteristic.

12. The method of claim 10 wherein:
the modulation in time is performed by varying a position of a mask relative to a position of a polychromator.

13. The method of claim 1 further comprising:
modulating the spectral transmission characteristic of said at least one measuring channel by means of an acousto-optical modulator and masks.

14. The method of claim 2 further comprising:
providing said reference channel with a substantially constant, non vanishing spectral transmission reference characteristic;

determining at said at least one measuring channel a reference output signal occurring at a no-sample condition and determining a reference output signal at said reference channel for the no-sample condition;

forming a quotient from said reference output signal of each of said at least one measuring channel and said reference output signal of said reference channel;

scaling said output signal of said reference channel with said quotient; and substracting said scaled output signal of said reference channel from the output signal of each of said at least one measuring channel.

15. The method of claim 14 further comprising:
normalizing a result of the substracting.

16. The method of claim 1 comprising:
categorizing mixtures of the substances quantitatively.

17. An apparatus for monitoring the presence of a preselected substance and/or property of a sample comprising:
at least one measuring channel including a filter having a predetermined spectral transmission characteristic throughout an entire spectral band of radiation inputted from said sample;

an optoelectrical converter for converting radiation transmitted through said filter into an electrical signal; and wherein the filter has a numerical spectral function specific to said preselected substance and/or property of said sample and generates an output signal dependent on said spectral distribution multiplied by said numerical spectral function; and the optoelectric converter integrates said output signal over a predetermined spectral band which is directly related to said preselected substance and/or property of said sample.

18. The apparatus of claim 17 further comprising:
at least one measuring channel and reference channel disposed in parallel to each other.

19. The apparatus of claim 18 wherein:
said at least one measuring channel and said reference channel are formed with one channel with said spectral transmission characteristic thereof being controllably variable in time.

20. The apparatus of claim 18 wherein:
said spectral transmission characteristic of said at least one measuring channel is implemented by a polarization interference filter.

21. The apparatus of claim 18 wherein:
said spectral transmission characteristic of said at least one measuring channel is implemented with an interference filter.

22. The apparatus of claim 18 further comprising:
a polychromator having masks disposed in a plane said radiation providing the spectral transmission characteristic of said at least two measuring channels.

23. The apparatus of claim 18 wherein:
at least one spectral transmission characteristic is implemented with a matrix having selectively controllable optical switches.

24. The apparatus of claim 23 wherein:
said matrix of selectively controllable optical switches comprises one of an LCD screen or a matrix of detectors which are selectively activated.

25. The apparatus of claim 18 wherein:

at least one spectral transmission characteristic is electronically controllable with respect to at least one of amplification and of spectral position.

26. The apparatus of claim 18 wherein:

at least one spectral transmission characteristic is electro-optically controllable.

27. The apparatus of claim 18 further comprising:

a mask and a polychromator disposed in said at least one measuring channel with the mask having a position which is controllably variable relative to the polychromator.

28. The apparatus of claim 18 further comprising:

an acousto-optical modulator and mask for controllably varying at least one of the spectral transmission characteristics.

29. The apparatus of claim 18 wherein:

the reference channel has a substantially constant transmission over the common spectral range of the spectral transmission characteristic of said at least one measuring channels.

* * * * *